United States Patent [19]

Tuompo et al.

[11] Patent Number: 5,910,420
[45] Date of Patent: Jun. 8, 1999

[54] METHOD AND TEST KIT FOR PRETREATMENT OF OBJECT SURFACES

[75] Inventors: Helena Tuompo, Espoo; Gun Wirtanen, Esbo; Satu Salo; Leena Scheinin, both of Espoo; Ari Batsman, Rusko; Seija Levo, Espoo, all of Finland

[73] Assignee: Orion-Yhtyma Oy Orion Diagnostica, Espoo, Finland

[21] Appl. No.: 09/054,822

[22] Filed: Apr. 3, 1998

Related U.S. Application Data

[63] Continuation of application No. PCT/FI97/00481, Aug. 18, 1997.

[30] Foreign Application Priority Data

Aug. 16, 1996 [FI] Finland .................................... 963235
Aug. 18, 1997 [FI] Finland ..................... PCT/FI97/00481

[51] Int. Cl.$^6$ .............................. C12Q 1/34; C12Q 1/40; C12Q 1/37; C12Q 1/54
[52] U.S. Cl. ............................ 435/18; 435/22; 435/23; 435/14; 435/24; 435/29; 435/975
[58] Field of Search ............................. 435/18, 22, 23, 435/14, 975, 29, 24

[56] References Cited

U.S. PATENT DOCUMENTS

| | | | |
|---|---|---|---|
| 4,419,248 | 12/1983 | Costerton | 435/29 |
| 5,258,100 | 7/1992 | Hollis et al. | 435/18 |
| 5,258,304 | 11/1993 | Carpenter et al. | 435/18 |
| 5,464,766 | 11/1995 | Bruno | 435/18 |
| 5,488,856 | 2/1996 | Dirk | 435/29 |

FOREIGN PATENT DOCUMENTS

| | | |
|---|---|---|
| 0590746A1 | 4/1994 | European Pat. Off. . |
| 2948791A1 | 6/1980 | Germany . |
| 3003766A1 | 8/1980 | Germany . |
| 92 13897 | 8/1992 | WIPO . |
| 96 01325 | 1/1996 | WIPO . |
| 96 33951 | 10/1996 | WIPO . |
| 9807883 | 2/1998 | WIPO . |

OTHER PUBLICATIONS

Bauer–Kreisel et al. (1996) *Appl. Envirn, Microbiol.* 39:913.
Costerton et al. (1981) *Ann. Rev. Microbiol.* 35:299.
Costerton et al. in *Bacterial Adhesion*, Savage et al., eds. Plenum Press, New York, p. 3–43 (1980).
Characklis (1990) in *Biofilms*, Characklis et al. eds. John Wiley & Sons, Inc., New York, pp. 523–584.
Characklis et al. (1990) in *Biofilms*, Characklis et al., eds, John Wiley & Sons, Inc., New York pp. 265–269.
Lee et al. (1996) *Infect. Immun.* 58:1628.
Nagata et al. (1995) *Biosci. Biotech Biochem.*, 59:2277.
Sjöberg et al. (1995) *Trans IChemE* 73:17.
Wirtanen (1995) *VTT Publications* 251 pp. 3, 4, 48.

*Primary Examiner*—Louise N. Leary
*Attorney, Agent, or Firm*—Baker & Botts

[57] ABSTRACT

The present invention provides a method for the pretreatment of object surfaces prior to taking a sample for microbial analysis. The method uses a blend to remove biofilms without hindering the growth of microorganisms. The method allows for reliable and replicable determination of microorganisms formed on the investigated surfaces.

49 Claims, No Drawings

METHOD AND TEST KIT FOR PRETREATMENT OF OBJECT SURFACES

This application is a continuation of PCT/FI97/00481, filed Aug. 18, 1997.

BACKGROUND OF THE INVENTION

The present invention concerns a method for the treatment of object surfaces prior to taking samples for microbiological investigations.

The invention concerns also a method for the pretreatment of object surfaces prior to cleaning.

The invention concerns also a test kit containing a sampler and a substance for the pretreatment of object surfaces.

Microorganisms, such as bacteria, yeast and mould fungi, attach readily to various surfaces. As they grow, they form layers called biofilms. There are various biofilms, often consisting of mixed populations of several different microbial species. The tendency of microbes to form biofilms can be seen as a survival strategy, through which they optimize the usage of the available nutrients. It is known that if microbes are allowed to form biofilms, it will be more difficult to cope with the health risks and pollution problems they cause. Within the shielding biofilm layer the microorganisms are able to efficiently resist the impact of antiseptics and antibiotics, and many patogenes are known to stay alive even for a long time with the protection of a biofilm (Costerton, J. W., Marrie. T. J. and Cheng, K.-J:, 1985. Phenomena of bacterial adhesion. In: Savage, D. C. and Fletcher, M. (Eds.) Bacterial Adhesion. New York: Plenum Press, p. 3–43).

Biofilms constitute a problem in many industrial fields. The problems they cause may be divided into two main groups: hygienic problems and problems affecting the production process per se. In the case of production that requires strict hygiene, even a slight microbial population may destroy the whole product. Slackened hygiene causes problems e.g. in food industry, in health care and in water supply systems. Other problems affecting the production process per se, such as formation of slime (mucus) in the apparatus and tubing, appear especially in wood and other processing industry, in air conditioning channels and even in desinfectant bottles. In some industrial areas microbes may even increase corrosion.

Biofilms formed by microorganisms, and the problems they cause, are, however, present also elsewhere than in industry, for instance on bathroom tiles, sauna benches, and in swimming and bubble pools.

If biofilms are allowed to form in food and process industry, the microbes they contain may pollute large amounts of product. Therefore hygienic monitoring is, or at least should be, used in most production plants. Often, however, the biofilm is found only when its become visible, and problems have already appeared, such as a functional disorder in the production unit, clogging of tubing or valves, or corrosion.

The biofilm consists mainly of water, 85–98%. In addition, the film contains polysaccharides and mineral collections formed by the microbes, and various dirt, depending on the environment (Costerton, J. W., Irvin, R. T. and Cheng, K.-J., 1981. The bacterial glycocalyx in nature and disease. Ann. Rev. Microbiol., 35, 299–324). When the circulation system works and water flows, the amount of biofilm is much larger than in the case of interrupted water circulation and an inspection of the dry tube surface. In a circulating liquid, a wet biofilm of 500 $\mu$m, may shrink to 2–5% of its total volume and to a thickness of 10–25 $\mu$m. Even if it is not necessarily visible, such a biofilm may increase friction and energy consumption in water circulation systems or in other tubings and plants. The structure of biofilms varies a lot, depending on the variation of surface materials, nutrients and microbes. This means also that there is no unique clear picture of their formation mechanism and exact structure. The biofilm structures must be determined separately for each case.

The biofilm can be found and studied by measuring its thickness and by dying the biofilm layer. Furthermore the microorganisms contained in the biofilm can be determined by taking a sample which is then cultivated on a growth medium.

The thickness of the biofilm is measured by various methods of analysis known as direct and indirect methods. The volumetric method is based on the determination of the wet weight, and the surface-mass-density methods are based on dry weight determinations. Furthermore the biofilms can be measured by microscopy, using light transmissivity, heat or electric conductivity, and oscillation. Most methods mentioned above are, however, difficult to perform in practical monitoring activities, because there are no user-friendly equipment (Characklis and Picologlou, 1978). Industry is interested in the source of the problem, not necessarily in the thickness of the biofilm.

Direct dying of biofilm on the surface of the tubing is potentially a good method to monitor its growth, but it is difficult to perform the dying in a closed tubing, because the dyes, often carcinogenic, enter the process, and the dyes per se may form precipitates, plus that they are difficult to remove. Therefore, it has been suggested that the biofilm be separated from its growing surface, after which the biofilm is dyed and its structure can be studied microscopically. In dying, it is possible to use various dyes, which attach to the polysaccaride chains, such as Alcian blue, toluide blue and erythrocine. From samples so dyed it has been found that biofilms that have been formed solely from microorganisms contain mainly polymers excreted by the microbes themselves, having structures consisting of complex polymers of various sugars.

Another method in use is the measurement of changes induced by the biofilm in heat conductivity and friction (Characklis, W. G. and Picologou, B. F. 1978. Measurement of the formation and destruction of primary biofouling films. In: Gray, R. H. (Ed.). Proceedings of the Ocean Thermal Energy Conversion (OTEC) Biofouling and Coosion Symposium. October 10–12, 1977. Seattle, Wash. Springfield Va., National Technical Information Service. p. 51–61.).

A monitor known as a biofilm monitor has been developed for finding and controlling biofilm. The monitor measures for example changes in pressure that may occur in a cooling equipment during flow. The change in pressure is proportional to friction, which, in its turn, is proportional to the friction of the cooling equipment. As in the indirect methods, such as those based on dying, inaccuracy has been a problem also of the monitors (Characklis, W. G. and Marshall, K. C. (Eds.). 1990. Biofilms. New York: John Wiley & Sons, Inc. 703 p.).

As mentioned above, the biofilms can be separated from the substrate by concentrated nitric acid In this case it is not possible to demonstrate and recognise the microorganisms by cultivation on a growthe medium, because said method destroys the microorganisms. The biofilm samples for microbial analysis have therefore in practice been taken with cotton swab, dipped in peptone saline solution, containing nutrients used by the microorganisms. Only small amounts of microorganisms can, however, be separated from the biofilm with the peptone saline solution, and the sampling surface still holds more than half of the biofilm after the swabbing.

The results above show that simpler and more user-friendly methods are needed for the detection of biofilms, especially in the process and air conditioning industry. In particular, methods are needed for checking whether the process surfaces are free from biofilms or not Biofilms constitute a special problem in the fields of industry mentioned above, and therefore the role of biofilms as a source of bacteria is being studied. In process hygiene, the assessment of a sufficient level of hygiene, and the attainment of this level, is of paramount importance. In the field of air conditioning there is a lack of knowledge concerning the influence of surface hygienic conditions on the amounts of microbes in the air.

Both in the process and air conditioning industry there is a need also to eliminate the disadvantages caused by the biofilms by cleaning and desinfecting the microbial growing surfaces, such as various tubing by strong desinfectants. Even strong desinfectants, however, are not necessarily able to remove the biofilms or to loosen their structures, so that the cleaning or desinfectant treatment would succeed.

SUMMARY OF THE INVENTION

It is an object of the present invention to clarify and eliminate the problems mentioned above, and to provide a new method for studying and observing biofilms prior to their becoming visible. It is a further object of the invention to provide a solution to the separation of biofilms and microorganisms from the studied surfaces in such a way that the microorganisms removed from the surface can be proved and determined.

It is a also an object of the present invention to provide a new method for the separation or the loosening of the attachment of biofilms and microorganisms from the various surfaces on which they grow in such a way that it is easier to remove the layers formed by microorganisms by washing.

The invention is based on the concept that the biofilm and the microorganisms are removed from the desired surface using suitable chemicals or mixtures of chemicals, which are spread on the surface prior to sampling or prior to the cleansing or desinfecting of the surface. Such a blend that repeatedly removes biofilms and microorganisms can be composed of substances, chemically effective in different ways.

The use of various detergents and enzymes in cleansing substances is known per se in the patent literature. For example, the DE Applications Nos. 2 948 791 and 3 003 766 disclose the use of polyethyleneglycol, anionic and cationic tensides and the enzymes, proteases, lipases and amylases of Bacillus, in stain removing agents and detergents at elevated temperatures to remove dirt. These publications do not, however, report the efficiency of the detergents in removing the microorganisms. Furthermore, the concentrations and the temperature of the effective substances (active agents) used are so high that bacteria and usually all microorganisms are destroyed as the dirt is removed. Said known compositions of detergents are thus not in themselves suitable for the monitoring of the surface hygiene. On the other hand bacterial powder containing enzymes has been suggested to be suitable for the opening of clogged sewage tubing, in U.S. Pat. No. 5,464,766. This known method is not, in its turn, suitable for the determination of microbes from the studied surfaces, since the mixture contains bacteria in itself The publication Nagata et al. (Nagata, A., Sakiyama, T., Itoh, H., Toyomasu, T., Enomoto, E., Nagai, T., Saeki, T. and Nakanishi, K, 1995, Comparative Study on Caustic and Enzymatic Cleanings of Stainless Steel Surface Fouled with β-Lactoglobulin, Biosci. Biotech Biochem. 59, 2277–2281) reports the cleaning of surfaces, artificially soiled with proteins, using alkaline agents and enzymes. The investigation concludes that the chemical substance is more effective the higher its concentration. Nagata et al. did not, either, investigate the detachment of microorganisms.

As opposed to the solutions presented above, in which detergents and enzymes have been used as microbicide washing solutions, or similar compositions, the present invention uses the detaching substances in such conditions, that the structure of the sample is loosened, and the removal of the sample from the surface is simplified, without killing the microbes. Thereby the biofilms can be studied and the microbes they contain can be determined, e.g., by cultivation.

Wirtanen (VTT Publications 251, Wirtanen, Gun: Biofilm formation and its elimination from food processing equipment) has put forward the idea that loosening the structure of the biofilm on the sampling surface by chemical treatment, might enhance the determination of the microorganisms. Furthermore, it has been suggested that the biofilm surface is treated with various detergent solutions, each separately, prior to taking a sample for microbial investigation with a sampler (Sjöberg, A-M et al., Transaction of the Institute of Chemical Engineers, vol 73, 1995, Cl, s. 17–21). The former publication does not, however, specify, what chemical methods should be used, and the latter reports the cleansability, i.e. assesses how much is left on the surface using each detergent separately, and does not at all determine what has been detached from the surface.

A combination of detergent and weak acid has been suggested for the treatment of the sampling surface prior to the immunological determination of the microorganisms (WO Application No. 96/1325), or a blend of detergent and enzyme to reveal the microorganisms at the surface prior to their determination by dying (U.S. Pat. No. 5,258,304). A combination of detergents and acids or enzymes may remove biofilms for the determination of microbes, but the microbes do not have to be alive in the determination methods mentioned in the publications.

Dilute acid or alkaline solutions are suggested to avoid the attachment of microbes to surfaces in liquid growth tanks (WO Application No. 92/13807), but the suitability for microbial analysis is not evaluated. Conditions least harmful for the microbes have been observed in the study.

In Chemical Abstracts vol 124, 170466 and in the original article Infect. Imun. (1996), 64, 1035–8, it has been shown how the proper enzyme of the bacteria *Streptococcus mutans* can be activated and how the bacteria can be made to detach from the biofilm and to decompose its own biofilm. This property is, in fact, proposed to be used to diminish the bacterial biofilm, and it is assumed that it is possibly suited only for the removal of said bacteria.

U.S. Pat. No. 5,128,100 aims at stopping the attachment of bacteria using cationic polymers without destroying the bacteria.

In the publication Bauer-Kreisel et al. (Appl. Env. Microbiol. Aug. 1996:3050–3052), NaCl, Tween, EDTA and Na-polyphosphate have been used separately to remove biofilm for immunological analysis of the microorganisms.

The EP Application No. 590 746 assesses the ability of proteases to release biofilms from surfaces, without determining the microbes, however.

It is apparent that different chemicals can be used to decompose the biofilm structure and the microbial amount can be estimated at least immunologically or by dying the biofilm left on the surface. The binding of microbes to surfaces can also be avoided without idestroying the microorganisms. This knowledge is all significant for maintaining clean surfaces in industry. At the moment, however, a method for a reliable analysis of the released microbe is still lacking. The present invention describes such a method for the analysis of microbes, whereby chemicals, such as a chelating agent, detergent, alcohol, amine, reducing substance and/or a hydrolytic enzyme/enzymes, are used to detach the microbial mass from the studied surface, so that the microbes can be quantitatively analysed from the detached microbe mass, without the amount of microbes being changed during the time of influence of the chemicals, and so that the growth of the microorganisms is not essentially hindered.

DESCRIPTION OF THE PREFERRED EMBODIMENTS

Thus, in the present invention, the studied surface is put into contact with an agent influencing the structure of the sample (e.g. microbial layer) at a pH suitable for the microorganisms. The surface is preferably contacted with a composition, which contains as active agent a chelating agent, detergent, alcohol, amine, reducing substance and/or a hydrolytic enzyme or a mixture of hydrolytic enzymes. According to a particularly preferred embodiment the composition contains at least two of the said substances in a physiological buffer solution The composition contains most preferably also a scuring or scrubbing agent to increase the amount of sample to be detached from the sampling surface.

The test kit according to the invention comprises a composition designed for the pretreatment of the sampling surface, containing as active agent (effective substance) a chelating agent, detergent, alcohol, amine, reducing substance and/or a hydrolytic enzyme or a mixture of hydrolytic enzymes in a physiological buffer solution, whereby the concentration of each active agent is 0.01–2.0 weight-%.

The invention provides a reliable sampling method, particularly well suited for hygienical monitoring. Particularly the present invention makes it possible to pretreat biofilms and similar environment samples containing microorganism layers, with a substance, which loosens up the structure of the sample, so that the biofilm and the microorganism better can be detached from their substrates, whereby the microorganisms accumulated at the studied surfaces can be analysed reliably and replicably. The invention is easy to apply with present analysis technique, whereby the microorganisms, after the detachment of the biofilm or microorganisms, can be determined by a method known per se, e.g. by cultivation on a contact plate, a dip slide, a growth dish or by other methods, such as microorganism ATP analysis, luminisence, impedance methods based on the change in electric conductivity, or by direct immunological methods, based on the antigenes of the microorganisms.

The method according to the invention is suitable for the removal of microorganisms from surfaces in the food industry, and in other process equipment and air conditioning, and also in various circumstances, in which there is a need for a continuous hygienic monitoring, such as in the proper monitoring of the food industry, and in hospitals, to assure that pathogenic bacteria are destroyed.

The method is suitable, for example, for the removal of microorganisms that spoil food and are detrimental to health, such as *Pseudomonas fragia, Listeria monocytogenesia, Candida utilista, Bacillus cereusta, Aspergillus niger,* and also other bacteria, yeast and mould fungi. These new treatment methods are replicably better suited than the traditional old peptone saline treatment for the detachment of microbes from microbial growths of different ages, of both single microorganisms and of mixed populations of several microorganisms.

At the same time as there is a need for reliable analysis of microbial samples from surfaces of the food industry and other industrial process equipment and from hospitals, it is also important to remove the microbes from these environments. Even strong cleansing, however, cannot destroy microbes that live sheltered by the biofilm on various surfaces.

The composition according to the present invention can thus be used also for the pretreatment of various surfaces prior to the cleaning desinfecting of the surfaces. The surface is put into contact with a composition that influences the structure of the sample, which substance contains as active agent a chelating substance, a detergent, alcohol, amine, a reducing agent and/or a hydrolytic enzyme or a mixture of hydrolytic enzymes. According to a specially preferred embodiment the composition contains at least two of said substances.

In the following the invention will be examined in greater detail with the aid of a detailed description and number of working examples. The embodiments are examples and they do not by any means limit the invention to these examples.

The term "object surface" refers in this invention to a sampling surface which has/has not microbial growth, or which has a layer formed by microorganisms, such as a biofilm, the microorganisms of which are to be determined quantitatively and/or qualitatively. Object surface denotes in this invention also a surface with a microbial growth layer, such as a biofilm, which is pretreated prior to cleaning and desinfecting.

The term "cleaning" refers in this invention to mechanical cleaning, sterilization with chemicals or heat, and desinfection. "Desinfectant" denotes in this invention desinfectants usually well known to professionals, which can be used to decrease the amonut of microbes at the object surface. The desinfectants may be inorganic or organic, acid, neutral or alkaline. Various chloride compounds (e.g., hypochlorite compounds, hydrogen peroxide) are examples of inorgic desinfectants, alcohol (e.g. methanol) and organic acids and bases are examples of organic desinfectants.

A "substance that influences the structure" of the sample, denotes in this invention a substance, which loosens the matrix of the microbial growth ground and decreases its adhesion to the studied surface. Such a substance may for example hydrolyse the polysaccaride chains of the matrix and decrease the hydrogen bonds between the chains. The substance may also make the matrix less hydrofobic, whereby it may more easily be transferred into the aqueous phase. Such substances are detergents, alcohols, amines, reducing substances and chelating agents. Many of the substances used in the invention are known, in high concentrations, to prevent the growth and propagation of microorganisms. For example, chelating agents bind the metals (Fe and Mn) needed for microbial metabolism, and alcohols are known to be microbicidal at concentrations over 50%. These substances are, however, used in such small amounts that the microorganisms do not die during the treatment. It is essential that the amount of the substance to be determined does not change during the time of treatment and that the growth of the microorganisms does not essentially stop. Therefore it has been noted in connection with the invention, that the concentration of each active agent of the composition is most preferably ca 0.01 to 2.0 weight-%.

In addition to detergents, alcohols, amines, reducing substances and chelating agents, the treatment composition can be augmented with a hydrolytic enzyme or a blend of hydrolytic enzymes, with the widest possible spectre, which for its part helps to gently detach the biofilm from its surface and improves the analytical determination sensitivity with respect to the microorganisms, but does not either destroy the microorganisms. The suitable enzymatic blend is selected depending on the specific application, since the surfaces may exhibit various dirt containing proteins, carbohydrates or fats, in addition to the bacterial biofilm.

On the basis of the description above, the composition according to the invention contains, for example:

a) 0–1.0 weight-% chelating agents, such as an aminotetracarboxylate, b) 0–2.0 weight-% detergents, such as non-ionic substance of the polyoxyethylene-type, non-ionic alkyl glucoside-type substance, ampholytic zwitterionic substance or anionic compound, c) 0–1.0 weight-% reducing substance, d) 0–1.0 weight-% alcohol, e) 0–1.0 weight-% amine, such as triethanolamine, f) 0–1.0 weight-% hydrolytic enzyme blend, with pectinase activity; pectinase and protease activity; pectinase, protease and amylase activity; pectinase and cellulase activity; amylase activity or amylase and papaine activity, and/or g) 0–1.0 weight-% a scouring or scrubbing agent, such as metasilicate, polyphosphate, phosphate or latex particles.

The most preferred concentrations of the above mentioned components are:

a, c - g: 0.01–0.95 weight-%, preferably 0.05–0.5 weight-%.

B: 0.01–1.95 weight - %, preferably 0.05–1.5 weight-%.

The pretreatment composition according to the invention comprises at least two of the components a–g, whereby the total concentration of the active agents is most suitably at most 3 weight-%, preferably at most 2.0 weight-%.

The activities of the enzymes used are preferably about 0.1–10.000 U/mg dry weight, whereby the preferred use of enzyme is ca 1 μg–100 mg/g (sample) dry weight.

Some examples of the substances used in the invention are listed below:

Chelating agents: inorganic and organic compounds. Inorganic complexing agents are various cyclic and linear phosphate compounds, for example polyphosphates, such as sodium polyphosphate ($Na_5P_3O_{10}$, STTP). Most important organic complexing agents are amine carboxyle acids and salts thereof, with acetic acid in the acid part (for example ethylenediaminetetraacetic acid (EDTA), n-hydroxyethyl ethylenediaminetetraacetic acid (HEDTA), diethylenetriaminepentaacetic acid (DTPA), nitriloacetic acid (NTA), ethylene diamine di-(o-hydroxy phenylacetic acid) (EDDHA), diethanol glycene (DEG) and ethanol diglycene (EDG), ethylene glycol bistetraacetic acid (EGTA) and salts thereof, in particular alkaline metal salts, hydroxy acids (glucone acid, glucone heptone acid and other saccarine acids, such as β-glucoisosaccarine acid, α-iso saccarine acid, tartaric acid, malic acid and citric acid) and salts thereof and organophosphates, with phosphatic acid in the acid part (for example amino trimethylene phosphonic acid (ATMP), 1-hydroxy ethylidene-1,1-diphosphonic acid (HEDP), ethylenediaminetetramethylene phosphonic acid EDTMP), diethylenetriaminepentamethylene phosphonic acid (DTPMP) and salts thereof.

Detergents: non-ionic polyoxiallylene substances, non-ionic alkyl glucoside substances, ampholytic zwitterionic substances and anionic and cationic compounds. Special examples of polyoxyalkylene substances are polyoxyalkylene mono- and trisorbitane esters (sorbitol and fatty acid esters of its anhydrides, copolymerized with ethyleneoxide). Examples of these are Polysorbate 80 (oleate ester), Polysorbate 20 (laureate ester), Polysorbate 40 (palmitate ester) and Polysorbate 60 (stearate ester). Examples of non-ionic substances are alkyl phenyl polyoxyethylene compounds (e.g., Triton® and Nonidet®) and octyl beta-D-glucopyranoside. Examples of ampholytic substances are betaine cocoa butter acid (e.g., DEHYTON®). Anionic substances are cholates (sodium taurocholate, sodium cholate, sodium deoxycholate and sodium glycocholate). Cationic compounds are, e.g., benzalkonium chloride and amphoteric surfactants are exemplified by sulphobetaines, such as N-dodecyl-N,N-dimethyl-2-ammonio-1-ethane sulphonate.

Amines: Suitable amines are, in particular, comprised of alkanolamines, such as mono-, di- or trialkanolamines, having an alkanol group comprising methanol, ethanol, propanol or isopropanol group.

Reducing agents: Suitable reducing agents are thiols and dithiols, which contain free SH-groups, such as N-acetyl-L-cysteine, L-cysteine, sodium thioglycolate, 2-mercaptoethanol, β-mercaptoethyleamine and dithiotreitole.

Hydrolytic enzymes: products, which contain pectinase activity, pectinase and protease activity, pectinase, protease and amylase acitivity, cellulase activity, hemicellulase activity, pectinase- and cellulase activity, amylase activity or amylase and papaine activity and mixtures thereof.

Alcohols: especially aliphatic alcohols, preferably isopropanol, hexanol, tridecanol, ethanol or methanol.

Scouring or scrubbing agents: silicates (e.g., sodium metasilicate), polyphosphates, phosphates and latexes.

The technical solution according to the invention can be used to detach samples of biofilm and microbes from process surfaces and similar surfaces, on which layers have formed by the action of microorganisms. The invention also makes it possible to determine whether the studied surface contains biofilm and/or microbes. Thus the invention is suitable for the investigation of environmental samples and biological materials. Significant applications are hygienic investigations in the area of health care (hospitals, medical centers) and in the medical, food, and fodder industries. These applications comprise both the microbial quality monitoring of the proper product, as well as the hygienic investigations of the facilities (i.a. tables, shelves, floors, walls, ceilings, sanitary equipment, sewage pipes) and process equipment (i.a machines, equipment, tubing, air conditioning tubes). Such investigations are increasingly performed in the medical, food and fodder industries (e.g., in bakeries, dairies, chark factories, butcheries, fodder mixing stations) and in forest industry.

According to the invention the treatment solution described above is applied to the sampling surface to be studied 0.001–1 ml, preferably ca 0.05–0.5 ml per square centimeter of the sample. The temperature of the pretreatment is 4°–45° C. and its duration 1–30 minutes.

As was mentioned above, the pH value of the treatment is set to a value suitable for microorganisms, whereby the initial range is from pH 4 to pH 8. During the treatment the pH value may change and increases often to close to 10–11. Treatment of a short duration at such a high pH value has usually not been detrimental. According to a preferred solution the active substances have been solved or suspended in a physiological buffer solution, e.g., citrate of triacetate buffer solution, with a pH value of 6–7. The concentration of the buffer solution is preferably 0.001–1 M, in particular 0.005–0.1 M.

The active substance is brought into contact with the sampling surface by wetting the surface with a solution of the active substance prior to sampling. Wetting can take place by spraying said solution on the sampling surface or by spreading the solution on the surface with a brush or a sampler. After pretreatment, a sample is detached from the surface. The sample is solved or suspended in an aqueous phase for investigation. In case the treatment composition contains scouring agents, scrubbing the surface with the sampler can detach the sample more efficiently.

After sampling, the sample can also be cultivated in nutrient agar or in liquid nutrient solution. According to an especially suitable application the pretreated sampling surface is brought into contact with a growth medium, on which it can be determined. A contact plate or dip slide is used as growth medium.

The sampling surface is preferably a biofilm produced by bacteria or other microorganisms. It should also be noted that a sample can be taken from a surface on which no biofilm has yet developed. When sampling surfaces containing mould fungi are to be sampled, the most preferred composition to be used comprises complexing agents, hydrolyzing enzymes and a scouring agent. As an example of a suitable product the following composition can be mentioned, which contains 0.05–1.0 weight-% EDTA, 0.1–1.0 weight-% of a mixture of pectinase, amylase and protease, and 0.1–1.0 weight-% sodium metasilicate.

When sampling surfaces with living bacteria and biofilm are to be sampled by swabbing, the composition to be used contains most preferably a complexing agent, a detergent, and a scouring agent. For example, the composition can contain 0.05–1.0 weight-% EDTA, 0.1–2.0 weight-% 4-(1, 1,3,3-tetramethylbutyl)phenol ethoxylate or polysorbate polyoxyethylene derivative and 0.1–1.0% sodium metasilicate.

Trietanol amine, a scouring agent and a detergent can be spread on a surface containing bacteria and biofilm by spraying.

The amount of microorganisms is determined from the sample, whereby the different microorganims are separated from the sample and determined separately. The microorganisms can also be found by determining their metabolites.

The sampler contained in the test kit comprises the pretreatment solution described above and a sampler with a swab, made of cotton, dacron, alginate or foam plastic, fastened into a suitable holder, e.g., a wooden or plastic stick or needle.

The application of the invention to the pretreatment of samples for microbiological investigation has been described above. It is evident, however, that the invention can be applied also to the treatment of samples for chemical (e.g. elemental analysis) and physical determination.

The composition according to the invention can also be used for pretreating various surfaces prior to cleaning and desinfecting. According to the invention the treatment solution described above is spread on the desired surface 0.001–1 ml, preferably ca 0.05–0.5 ml per square centimeter of the sample. The treatment temperature can be the same as in pretreating the surface for sampling, i.e., 4–45° C. and the duration of the treatment 1–30 minutes.

If the surface is pretreated prior to cleaning and desinfecting, and the purpose is not to take microbial samples, the initial pH value of the treatment does not have to be suitable for the microorganisms, but usually the pH range 4–8 is used, which allows the enzymes to be active. According to a preferred alternative, the active substances are solved or suspended in a physiological buffer solution, e.g., citrate or triacetate buffer solution, with a pH value of 6–7. The concentration of the buffer solution is most suitably 0.001–1 M, preferably 0.005–0.1 M.

The active substance is brought into contact with the desired surface by wetting the surface with a solution of the active substance prior to cleaning or desinfecting. The wetting can be done by spraying said solution on the surface or by spreading the solution on the surface with a brush. After the pretreatment the surface is washed or desinfected in the usual way. When the treatment solution contains scouring agents, scrubbing the surface can make the removal of microbes more efficient prior to washing and desinfecting. The composition designed for the pretreatment prior to cleaning and desinfecting comprises the same active substances as the composition used for pretreatment prior to sampling.

The following examples clarify the invention.

Abbreviations

ATP: adenosine triphosphate

Brij 35: polyoxyethylene laurylether

CHAPS: 3,3,-cholamidopropyl dimethyl ammoniol-1-propane sulphonate

CHAPSO: 3,3,-cholamidopropyl dimethyl ammoniol-2-hydroxypropane sulfonate

EDTA: ethylene diaminetetraacetic acid

EGTA: ethylglycol bisaminoethylether tetracetic acid

RLU: relative light releasing unit

SDS: sodium dodecyl sulphate

Triton-X-100: octyl phenoxypolyetoxy ethanol

Tween 80: polyoxyethylenol sorbitol acid

RBS: washing agent containing alkaline tensides cfu: colonies forming unit

Methods used

In this invention the biofilms have been cultivated and the removed bacteria have been determined by cultivating on dishes and dip slides (Wirtanen, G. 1995. Biofilm formation and its elimination from food processing equipment, Espoo: The Technical Research Centre of Finland. VTT Publications 251, 106 p.+app. 48 p.) and with the ATP-method (ATP-determination kit, Bio Orbit). The bacteria and the amount of biofilm left on the surface after treatment have been estimated by image analysis (Wirtanen. G. and Mattila-Sandholm, T. 1994. Measurement of biofilm of *Pediococcus pentosaceus* and *Pseudomonas fragi* on stailess steel surfaces. Colloids and Surfaces B: Biointerfaces, 2, 33–39.)

Chemical substances and enzymes used

Chelating agents: EDTA, EGTA

Amines: trietanol amine

Alcohol: isopropanol

Reducing agents: N-acetyle-L-cysteine (in the following abbreviated "acetyl cysteine") and ditiotreitole Detergents: Triton-X-100, octyl glucoside, SDS, CHAPS, CHAPSO, BRIJ 35

Hydrolytic enzymes: pectinase E.C.3.2.1.15, protease E.C.3.4.21.62, amylase E.C.3.2.1.1, cellulase E.C.3.2.1.4, papaine E.C.3.4.22.2.

EXAMPLE 1

Pretreatment of biofilm and sampling

Cultivation of biofilm in liquid

Sheets of stainless steel, AISI 304/2B, were used for the biofilm growth surface. The steel sheets were washed with 2% RBS washing solution having the temperature 50° C., in which the sheets were shaken for 20 minutes (75 shakings per minute). The sheets were rinsed five times with doubly distilled water of 45° C., shaking as above for five minutes, whereafter the sheets were autoclaved.

*Pseudomonas fragi*-bacteria (ATCC 4973) were used to form the biofilm. The bacteria were kept at −80° C. The bacteria were awakened prior to use in Iso-Sensitest Broth solution (Oxoid).

The biofilm was cultivated on cleansed steel sheets (ca 10 sheets), having the size of an object glass (18.75 $cm^2$), in 25° C., usually for 5 days in 200 ml broth solution (2.4 g LAB-Lemco pouwder (OXOID), 8 g Nutrient broth powder (Difco), 50 g saccarose (BDH), 10 g glucose (BDH) and 10 g fructose (Merck) in a liter of distilled water), into which 2 ml bacterial solution was transferred, with a cell concentration of $10^7$–$10^9$ cells/ml. The growth pans were shaken at a speed of 60 shakes per minute and a new broth solution, without bacteria, was introduced every other day.

After cultivation the steel sheets with their biofilms were rinsed twice with distilled water prior to the biofilm removal experiments. In the treatments either the investigated mixture or a swab stick of cotton, dacron or alginate wet in pepton saline was scrubbed against the biofilm surface and the biofilm attached to the sampler was suspended in pepton saline (1 g pepton/l±8.5 g NaCl/l), from which a dilution series was made. About 0.2 ml of the investigated mixture had been imbibed in the sampler. After this the bacteria that had been removed by the suspension were cultivated on nutrient agar and grown for two days at 25° C. prior to counting the colonies. The treated sheets were dyed with 0.1% acridine orange (BDH). The biofilm left on the surface took on a greenish colour and the amount of biofilm was quantified by image analysis in fluorescence microscope. The microbes left on the surfaces took simultaneously on a yellow colour.

Cultivation of biofilm in currents of air

The capability of a cotton swab, wet by combinations of removing substances, to detach mould fungi, *Aspergillus niger*, of various ages and their biofilms from steel surfaces in air conditioning equipment was assessed in the following way:

First, *Aspergillus niger* mould was precultivated in a Sabouraud vessel, and the spores were mixed into a suspension. The suspension was spread on steel surfaces covering the whole area. The sheets were incubated at 25° C., in stable air current, at 70% relative humidity for various times. After 14 and 28 days the sheets were analysed by cultivation in a Sabourad vessel and again by image analysis.

EXAMPLE 2

The capability of chelating agents to remove bacteria and biofilms

The capability of different chelating agents to remove bacteria and biofilms from surfaces was investigated using the biofilm formed by *Pseudomonas fragi* on steel surfaces as a model. The biofilm was removed with swabs manufactured of different materials. The swab sticks had been wet in peptone saline solution (0.85 weight-% NaCl, control) and in treatment solutions containing chelating agents.

The results are given in Table 1.

Table 1

Capability of chelating agents to detach bacteria and biofilms

| Active agent % (g/g)* | Amount of bacteria removed from surface, log cfu/$cm^2$ | Amount of biofilm left on surface after treatment, % of total area |
|---|---|---|
| Peptone saline solution and cotton swab | 6.4 | 40 |
| Peptone saline solution and dacron swab | 6.6 | 42 |
| Peptone saline solution and alginate swab | 6.5 | 45 |
| 0.1% EDTA and cotton swab | 7.0 | 49 |
| 0.2% EDTA and cotton swab | 5.5 | 22 |
| 0.4% EDTA and cotton swab | 7.0 | 16 |
| 0.6% EDTA and cotton swab | 6.5 | 28 |
| 0.4% EGTA and cotton swab | 6.5 | 62 |
| 0.6% EGTA and cotton swab | 6.9 | 43 |
| 0.8% EGTA and cotton swab | 7.5 | 50 |

*concentration as % in 0.02 M tris-acetate buffer, pH 7.75

The choice of sampler: cotton swab, dacron or alginate swab, did not make any difference for the amount of bacteria removed or the amount of biofilm left after treatment. Of the chelating agents, EDTA was the most efficient in removing biofilms in concentrations 0.2–0.6%. The amount of bacteria removed from the surface varied between 5.5–7.0 log units.

EXAMPLE 3

The capability of active agents imbibed in a cotton swab to detach bacteria from biofilms Table 2 gives the results of experiments with triethanol amine, isopropanol and triethanol amine and the latter mixture with reducing agents, i.e., acetyl cysteine or ditiotreitol, added, to remove biofilm formed by *Pseudomonas fragi*. A rayon swab, commonly used in ATP-determinations, was used in the determinations, wetted in the active substance. The table shows the results of the bacterial cultivation after removal and the bacterial ATP analysis, describing the bacteria removed from the surfaces, when the surfaces had been treated with combinations of the different substances. The biofilm left on the surfaces was determined from the same sheets. The experimental set-up was the same as in Example 1 and the removed bacteria were analysed by cultivation and by ATP determination (ATP-determination kit, BioOrbit). The amount of the biofilm left on the surface was assessed by image analysis according to Example 1.

TABLE 2

Substances for the removal of biofilm formed by *Pseudomonas fragi*; results of bacterial cultivation and bacterial ATP-analysis after removal

| Active mixture % (g/g) | Amount of bacteria removed log cfu/$cm^2$ | Amount of bacteria removed, ATP anal. RLU/$cm^2$ | Amount of biofilm left on surfaces % of total area |
|---|---|---|---|
| Peptone saline solution | 5.1 | 5.1 | 76 |
| 0.02% Triethanol amine* | 6.7 | 4.1 | 77 |
| 0.02% Triethanol amine, 0.02% Isopropanol* | 6.4 | 4.2 | 66 |
| 0.02% Triethanol amine, | 7.1 | 7.2 | 55 |

TABLE 2-continued

Substances for the removal of biofilm formed by *Pseudomonas fragi*; results of bacterial cultivation and bacterial ATP-analysis after removal

| Active mixture % (g/g) | Amount of bacteria removed log cfu/cm² | Amount of bacteria removed, ATP anal. RLU/cm² | Amount of biofilm left on surfaces % of total area |
|---|---|---|---|
| 0.02% Isopropanol, 0.01% Acetylcysteine* 0.02% Triethanol amine, 0.02% Isopropanol, 0.01% Ditiotreitol* | 4.8 | 7.2 | 47 |

*0.02 M Tris-acetate buffer, pH 7.75

The combination of triethanol amine, isopropanol and acetyl cysteine was most efficient in removing bacteria and biofilm. By ATP-analysis it was seen that mixtures according to the invention, with reducing agents added to alcohols or amines, are efficient in removing both biofilms and bacteria. It can also be seen, that alcohol, such as isopropanol, and amine, such as triethanol amine, influence the amount of cultivated bacteria. On the other hand, they do not remove biofilm well enough on their own. Together with reducing agents, they do, however, remove both bacteria and biofilm well.

EXAMPLE 4

The capability of various detergents to remove bacteria in combination with a chelating agent and a reducing substance The capability of various detergents to remove bacteria in combination with a chelating agent, EDTA, and a reducing substance, ditiotreitol, was compared by cultivating. Image analysis was used to determine the capability of the same mixtures to remove biofilm. The experiments were set up according to example 1.

TABLE 3

Removal of *Pseudomonas fragi* biofilm from steel surfaces with a swab wet with combinations of detergent, chelating agent and reducing substance

| Active agent % (g/g) | Properties of detergent | Amount of bacteria removed log cfu/cm² (SD) | Biofilm left on surface % of area (SD) |
|---|---|---|---|
| mixture* | chelating and reducing | 5.23 ± 0.38 | 15.1 ± 3.0 |
| 1.0% Triton-X-100* | non ionic | 3.96 ± 0.30 | 20.1 ± 6.2 |
| 10% Triton-X-100* | non ionic | 4.56 ± 0.02 | 64.8 ± 7.1 |
| 1.0% octyle glucoside | non ionic | 3.43 ± 0.00 | 31.2 ± 4.5 |
| 1.0% SDS* | anionic | 4.00 ± 0.17 | 9.7 ± 5.2 |
| 1.0% CHAPS* | ampholytic | 3.52 ± 0.11 | 29.7 ± 17.5 |
| 1.0% CHAPSO* | ampholytic | 4.2 ± 0.34 | 19.2 ± 2.1 |
| 1.0% BRIJ 35* | non ionic | 4.61 ± 0.32 | 11.9 ± 6.9 |

0.01 M tris-acetate buffer, pH 7.75, in which 0.07% EDTA and 1% ditiotreitol

Although the additions of detergent did not significantly increase the removal of bacteria from the surfaces, the replicability of the determination of the removed bacteria was better, however, with the use of detergents, as can be seen from the smaller variation of these results. Some detergents, such as the anionic detergent SDS and the non-ionic detergent BRIJ 35, were more successful in removing biofilm than a mixture of only EDTA and ditiotreitol.

EXAMPLE 5

Effect of hydrolytic enzymes on biofilms

The effect of hydrolytic enzymes on biofilms is shown in Table 4; the experiments were set up as in Example 1. The biofilm surface was treated with a swab wet with one or several enzymes.

TABLE 4

The effect of hydrolytic enzymes on the removal of *Pseudomonas fragi* and its biofilm

| Enzyme and its amount in the mixture % (g/g) | Enzyme quality | Amount of bacteria removed log cfu/cm² | Share of surface covered by biofilm |
|---|---|---|---|
| Peptone saline solution | | 6.4 | 40 |
| 0.16% pectinase* | Orion Diagnostica** | 5.6 | 22 |
| 0.16% pectinase, 0.16% protease | Orion Diagnostica** | 6.3 | 18 |
| 0.16% pectinase, 0.16% protease, 0.16% amylase | Orion Diagnostica** | 7.0 | 49 |
| 0.16% pectinase, 0.16% cellulase | Orion Diagnostica**, Sigma, 0.3 U/mg dry w. | 5.9 | 10 |
| 0.16% amylase | Sigma, 1500–3000 U/mg dry weight | 5.4 | 11 |
| 0.08% amylase | Sigma, 1500–3000 U/mg dry weight | 6.7 | 38 |
| 0.08% papaine* | Sigma, 1–2 U/mg dw | | |

*0.01 M tris-acetate buffer, pH 7.75, in which 0.1% EDTA
**cleansed and activities determined at Orion Diagnostica, Kaisu Ollila, Teesside University, England, 1995

The above results show that the mixture of pectinase, protease and amylase was the best of the enzyme mixtures in removing bacteria. Compared with only peptone saline, the aforementioned mixture performed 0.6 log units better. Sole pectinase, the mixture of pectinase and protease, or pectinase and cellulase, and sole amylase were 2 to 4 times more successful in removing biofilm than treatment with only peptone saline. Furthermore it can be observed, that several hydrolytic enzymes remove biofilm well without destroying the bacteria

EXAMPLE 6

The capability of various mixtures to remove biofilms of different ages

The capability of the mixtures tested in Example 5 to remove biofilms and moulds of different ages from cultivations in aerobic atmosphere was also tested. For this purpose, a swab was wet in the various combinations of the releasing substances. The swab stick was used to remove *Aspergillus niger* moulds of different ages, and biofilms formed by these fungi from steel surfaces in air conditioning equipment. The removal capability of the swab wet in the different mixtures was determined.

Three surfaces were treated in parallell in order to assess the replicability of the methods.

TABLE 5

The capability of a swab wet in selected mixtures to remove spores and biofilm of *Aspergillus niger* mould from young, 14 days old, and older, 28 days old, biofilm

| Active agents and their concentrations in % (g/g) | Amount of biofilm left on surface in % of total area (SD), 14 days | The amount of cells left on surface % (SD), 14 days | Amount of biofilm left on surface in % of total area (SD), 28 days | The amount of cells left on surface % (SD), 28 days |
|---|---|---|---|---|
| Peptone saline solution | 64.2 ± 43.9 | 6.6 ± 10.6 | 28.9 ± 23.8 | 2.4 ± 3.8 |
| 0.2% Tween 80 0.9% NaCl in water | 28.4 ± 37.9 | 2.2 ± 1.8 | 51.3 ± 27.5 | 2.9 ± 3.5 |
| 0.2% Tween 80 0.9% NaCl 1.0% Triton-X-100 | 28.0 ± 38.6 | 1.9 ± 2.5 | 12.3 ± 10.4 | 0.1 ± 0.1 |
| 0.2% isopropanol, 0.2% triethanol amine* | 42.1 ± 34.6 | 2.3 ± 2.7 | 38.6 ± 32.0 | 4.6 ± 5.2 |
| 0.2% isopropanol, 0.2% triethanol amine, 0.3% Na-metasilicate | 31.1 ± 8.7 | 3.7 ± 0.4 | 47.8 ± 39.8 | 6.6 ± 7.4 |
| 0.2% isopropanol, 0.2% triethanol amine, 1.0% Triton-X-100* | 38.0 ± 40.8 | 2.2 ± 2.6 | 14.0 ± 21.8 | 0.1 ± 0.2 |
| 0.2% isopropanol, 0.2% triethanol amine, 0.3% Na-metasilicate 1.0% Triton-X-100* | 43.1 ± 16.4 | 1.9 ± 0.9 | 53.8 ± 30.1 | 4.8 ± 3.9 |
| 0.1% EDTA, 0.4% enzyme blend**,* | 35.7 ± 50.6 | 6.1 ± 10.0 | 32.6 ± 44.1 | 3.7 ± 6.1 |
| 0.1% EDTA, 0.4% enzyme blend**, 0.3% Na-metasilicate | 23.6 ± 10.3 | 2.3 ± 1.6 | 17.3 ± 11.6 | 1.5 ± 1.3 |
| 0.1% EDTA, 0.4% enzyme blend**, 1.0% Triton-X-100* | 24.1 ± 20.6 | 2.0 ± 2.6 | 32.7 ± 7.9 | 3.0 ± 2.4 |
| 0.2% isopropanol 0.2% triethanol amine 0.3% Na metasilicate | 34.4 ± 16.1 | 1.0 ± 0.5 | 6.9 ± 7.7 | 0.2 ± 0.3 |

*0.02 M tris-acetate buffer, pH 7.75
**the enzyme blend was the mixture of pectinase, amylase and protease described in Example 5

All mixtures according to the invention removed biofilms and mould cells of two weeks old moulds more efficiently than peptone saline. Older, one month old, biofilms and mould cells were more efficiently removed with Triton-X-100 added to a treatment mixture of isopropanol and triethanol amine or Tween.

A comparison of the results of Tables 5 and 1 shows that the addition of enzymes increases the efficiency of a blend containing chelating agents.

A scouring agent, Na-metasilicate, was efficient in removing biofilm together with a chelating agent, EDTA (i.e., aminotetracarboxylate) and enzymes.

On the basis of the results in Table 5 it is seen that an especially suitable combination for the removal of mould fungi comprises a chelating agent, such as EDTA, an enzyme blend and a scrubbing agent, such as Na meta silicate.

EXAMPLE 7

Mixtures of active agents

Compositions that performed well in removing biofilms formed by bacterial mixtures were selected from Table 5 on the basis of the previous examples. The compositions were applied on biofilm, either by swabbing or spraying (0.2 ml/cm$^2$), whereafter their capabilities to remove selected bacteria were determined. The bacteria were detached from the surfaces according to Example 1 and were cultivated on Pseudomonas nutrient agar, on Listeria sheep blood agar and Bacillus nutrient agar. The results are given in Table 6.

TABLE 6

Removal of co-growth of the *Pseudomonas fragi*, *Listeria monocytogenes* and *Bacillus cereus* bacteria by swabbing or spraying; and the amount of bacteria in cultivation

| Blend of active agents, concentrations % (g/g) | Amount of *Pseudomonas fragi* log cpu/cm² | | Amount of *Listeria monocytogenes* log cpu/cm² | | Amount of *Bacillus cereus* log cpu/cm² | |
|---|---|---|---|---|---|---|
| | swabbing | spraying | swabbing | spraying | swabbing | spraying |
| Peptone saline solution | 4.3 | 3.8 | 5.5 | 5.0 | — | — |
| 0.2% Tween 80 0.9% NaCl in water 1.0% Triton-X-100* | 3.9 | 4.9 | 4.6 | 5.0 | — | — |
| 0.2% Triethanol amine, 0.3% Na metasilicate 1.0% Triton-X-100* | 2.9 | 5.4 | 4.1 | 5.5 | — | — |
| 0.1% EDTA, 0.3% Na metasilicate 1.0% Triton-X-100* | 3.7 | 4.9 | 4.5 | 5.4 | — | — |

*0.02 M trisacetate buffer, pH 7.75

Spraying with a detergent solution to remove bacteria gave a better yield of cultivation than removing by swabbing. For Pseudomonas the difference was 1–2 log units and for Listeria 1 log unit. There was not enough *Bacillus cereus* for cultivation.

EXAMPLE 8

Removal of biofilm by swabbing or spraying

*Pseudomonas fragi*, *Listeria monocytogenes* and *Bacillus cereus* bacteria formed a co-growth. The amount of the growth was assessed by image analysis. After swabbing and spraying (0.2 ml/cm²) the amounts of bacteria and cells left on the steel surfaces were determined according to the instructions in Example 1.

TABLE 7

Amounts of bacteria and biofilms left on steel surfaces after swabbing and spraying

| Blend of active agents, concentrations % (g/g) | Amount of biofilm left on surface, % of total area | | Amount of cells left on surface % | |
|---|---|---|---|---|
| | swabbing | spraying | swabbing | spraying |
| Peptone saline solution | 94 | 30 | 11 | 1 |
| 0.2% Tween 80 0.9% NaCl in water 1.0% Triton-X-100* | 53 | 17 | 2 | 1 |
| 0.2% triethanol amine 0.3% Na-metasilicate 1.0% Triton-X-100* | 80 | 7 | 16 | 1 |
| 0.1% EDTA 0.3% Na-metasilicate 1.0% Triton-X-100* | 48 | 37 | 4 | 3 |

*0.02 M trisacetate buffer, pH 7.75

Spraying the blend of active agents is the most effective way of removing biofilm from steel surfaces, as can be seen from the results above. Spraying peptone saline solution decreases the amount of biofilm to one third and the amount of cells to one tenth. The amount of biofilm left on the surface was one tenth of the original amount after spraying with a blend of Triton-X-100, triethanol amine and sodium metasilicate. Spraying on the surface of the biofilm made the removal more efficient, without damaging the bacteria.

Examples 7 and 8 report the results of one and the same experiment. Swabbing with a mixture of a chelating agent, e.g., EDTA, and a scouring agent, e.g., Na-metasilicate in a trisacetate buffer containing Triton-X-100, is a very efficient way of removing living bacteria and biofilm, as can be seen from the results of the experiment reported in Examples 7 and 8. With the spraying treatment, living bacteria and biofilm were very efficiently removed by a mixture of triethanol amine and a scouring agent in a trisacetate buffer containing Triton-X-100.

We claim:

1. A method for the pretreatment of an object surface prior to taking a sample for microbial analysis of microorganisms present on the surface, comprising bringing the object surface, at a pH-value suitable for the microorganisms, into contact with a substance which contains as active agent at least one of a chelating agent, a detergent, an alcohol, an amine, a reducing substance, a hydrolytic enzyme or a mixture of hydrolytic enzymes, at a concentration sufficient for detaching the microorganisms from the studied surface so that the amount of substance to be determined does not change during the influence time and that the growth of microorganisms is not essentially hindered.

2. The method according to claim 1, wherein the surface is brought into contact with a composition, which contains at least two of the said active agents in a physiologic buffer solution.

3. The method according to claim 1, wherein a composition is used, which further contains a scouring agent to increase the amount of sample removed from the object surface.

4. The method according to any one of the preceding claims, wherein a composition is used, in which the concentration of each of the active agent is 0.01–2.0 weight-%.

5. The method according to claim 4, wherein 0.001–1 ml. of solution is used per square centimeter of the sample.

6. The method according to claim 1, wherein the surface is brought into contact with the active agent at 4–45° C., for 1–30 minutes, at pH 4–8.

7. The method according to claim 4, wherein the composition contains the active agents in a triacetate buffer solution, which pH value is 4–8.

8. The method according to claim 1, wherein the active agent is brought into contact with the sampling surface by wetting the surface with a solution of the active agent prior to taking a sample from the surface.

9. The method according to claim 8, wherein the active agent is sprayed on the sampling surface prior to sampling.

10. The method according to claim 1, wherein EDTA is used as chelating agent.

11. The method according to claim 1, wherein a non-ionic polyoxyethylenic substance, a non-ionic alkyl glucosidic substance, an ampholytic zwitterionic substance or an anionic compound is used as detergent.

12. The method according to claim 1, wherein triethanol amine is used as active agent.

13. The method according claim 1, wherein the active agent is a hydrolytic enzyme blend, which contains at least one of pectinase activity; pectinase and protease activity; pectinase, protease and amylase activity; pectinase and cellulase activity; amylase activity; or amylase and papaine activity.

14. The method according to claim 1, wherein at least one of silicate, polyphosphate, phosphate or latex is used as scouring agent.

15. The method according to claim 1, wherein the sampling surface is a biofilm produced by bacteria or other microorganisms.

16. The method according to claim 1, wherein it is investigated, whether the sampling surface contains microorganisms or biofilm produced by microorganisms.

17. The method according to claim 1, wherein the amount of microorganisms is determined from the sample.

18. The method according to claim 1, wherein the microorganisms are separated and determined separately from the sample taken from the sampling surface.

19. The method according to claim 1, wherein metabolites of the microorganisms are determined from the sample taken from the sampling surface.

20. The method according to claim 1, wherein a microbial ATP-determination is performed for the sample taken from the sampling surface.

21. The method according to claim 1, wherein the concentration of the sample removed from the sampling surface is determined.

22. The method according to claim 1, wherein the pretreated object surface is brought into contact with a growing substrate, from which the microbes can be determined.

23. The method according to claim 22, wherein the growth medium comprises a contact plate or dip slide.

24. The method according to claim 1, wherein the sample consists of an environmental sample or biological material.

25. A method for the pretreatment of object surfaces prior to cleaning, comprising contacting the object surface with a substance, which contains as active agent at least one of a chelating agent, a detergent, an alcohol, an amine, a reducing substance or a hydrolytic enzyme or a blend of hydrolytic enzymes, at a concentration which is sufficient for removing microbes from the object surface without inhibiting the growth of the microbes, and washing the microbial layer thereafter.

26. The method according to claim 25, wherein the surface is brought into contact with a composition which contains at least two of said substances.

27. The method according to either of claims 25 or 26, wherein a composition containing a scouring agent is used.

28. The method according to claim 25, wherein a composition is used, in which the concentration of each active agent is 0.01–2.0 weight-%.

29. The method according to claim 28, wherein ca 0.001–1 ml of the solution is used per square centimeter of the object surface.

30. The method according to claim 25, wherein the surface is brought into contact with the active agent at 4–45° C., for 1–30 minutes.

31. The method according to claim 28, wherein the composition contains the active agents in a triacetate buffer solution, with a pH value of 4–8.

32. The method according to claim 25, wherein the active agent is brought into contact with the object surface by wetting the surface with a solution of the active agent prior to cleaning or desinfecting.

33. The method according to claim 32, wherein the active agent is sprayed on the surface.

34. The method according to claim 25, wherein EDTA is used as chelating agent.

35. The method according to claim 25, wherein at least one of a non-ionic polyoxyethylenic substance, a non-ionic alkyl glucosidic substance, an ampholytic zwitterionic substance or an anionic compound is used as detergent.

36. The method according to claim 25, wherein triethanol amine is used as active agent.

37. The method according to claim 25, wherein the active agent is a hydrolytic enzyme blend, which contains at least one of pectinase activity; pectinase and protease activity; pectinase, protease and amylase activity; pectinase and cellulase activity; amylase activity; or amylase and papaine activity.

38. The method according to claim 27, wherein silicate, polyphosphate, phosphate or latex is used as scouring agent.

39. The method according to claim 25, wherein the sampling surface is a biofilm produced by bacteria or other microorganisms.

40. A test kit for taking samples from an object surface, which kit comprises a sampler and a composition for the pretreatment of the object surface, wherein the composition contains as active agent a chelating agent, a detergent, an alcohol, an amine, a reducing substance, a hydrolytic enzyme or a blend of hydrolytic enzymes in a physiological buffer solution, and wherein the concentration of each active agent is 0.02–2.0 weight-%.

41. The test kit according to claim 40, wherein the composition contains at least two active agents and its pH value is 4–8.

42. The test kit according to claim 40 or 41, wherein the composition further contains a scouring agent.

43. The test kit according to claim 40, wherein the composition contains at least two of
 a) 0–1.0 weight % aminotetracarboxylate,
 b) 0–2.0 weight % non-ionic polyoxyethylenic substance, non-ionic alkyl glucosidic substance, ampholytic zwitterionic substance or anionic compound,
 c) 0–1.0 weight % reducing agent,
 d) 0–1.0 weight % alcohol,
 e) 0–1.0 weight % triethanol amine,
 f) 0–1.0 weight % hydrolytic enzyme blend, which contains pectinase activity, pectinase and protease activity, pectinase, protease and amylase activity, pectinase and cellulase activity, amylase activity and amylase and papaine activity or
 g) 0–1.0 weight % silicate, polyphosphate, phosphate or latex.

44. The test kit according to the claim 43, which is designed for taking samples from object surfaces containg mould fungi, wherein the composition contains components a, f and g or a, d, f and g.

45. The test kit according to claim 44, wherein the composition contains 0.05–1.0 weight % EDTA, 0.1–1.0 weight % pectinase, amylase and protease blend, and 0.1–1.0 weight % sodium metasilicate.

46. The test kit according to claim 43, which is designed for taking samples from object surfaces containing living bacteria and biofilm, wherein the composition contains the components a, b and g or a,b,c,d and g.

47. The test kit according to claim 46, wherein the composition contains 0.05–1.0 weight % EDTA, 0.1–2.0 weight % ethoxylate of 4-(1,1,3,3,-tetramethylbutyl)phenol or polyoxyethylene derivative of polysorbate and 0.1–1.0% of sodium metasilicate.

48. The test kit according to any one of claims 40 to 47, wherein the solvent of the composition is 0.001–0.1 M trisacetate buffer solution.

49. The test kit according to one of the claims 40 to 47, wherein the sampler comprises a cotton swab, dacron, alginate or foam plastic, which is fastened to a suitable holder.

* * * * *